(12) United States Patent
Steffen et al.

(10) Patent No.: US 10,750,944 B2
(45) Date of Patent: Aug. 25, 2020

(54) EYE SURGERY VISUALIZATION SYSTEM

(71) Applicant: Carl Zeiss Meditec AG, Jena (DE)

(72) Inventors: Joachim Steffen, Westhausen (DE); Christoph Hauger, Aalen (DE)

(73) Assignee: Carl Zeiss Meditec AG, Jena (DE)

(*) Notice: Subject to any disclaimer, the term of this patent is extended or adjusted under 35 U.S.C. 154(b) by 107 days.

(21) Appl. No.: 16/129,610

(22) Filed: Sep. 12, 2018

(65) Prior Publication Data

US 2019/0076020 A1 Mar. 14, 2019

(30) Foreign Application Priority Data

Sep. 12, 2017 (DE) .................. 10 2017 121 085

(51) Int. Cl.
*A61B 3/13* (2006.01)
*A61B 90/00* (2016.01)
*A61B 34/20* (2016.01)
*G06T 7/73* (2017.01)
*G02B 21/00* (2006.01)
*A61B 3/00* (2006.01)

(52) U.S. Cl.
CPC .............. *A61B 3/13* (2013.01); *A61B 3/0058* (2013.01); *A61B 34/20* (2016.02); *A61B 90/361* (2016.02); *G02B 21/0012* (2013.01); *G06T 7/74* (2017.01); *A61B 3/132* (2013.01); *A61B 2034/2055* (2016.02); *G06T 2207/10056* (2013.01)

(58) Field of Classification Search
CPC ........... A61B 3/14; A61B 3/0025; A61B 3/12; A61B 3/102; A61B 3/0058

USPC ......................................................... 351/205
See application file for complete search history.

(56) References Cited

U.S. PATENT DOCUMENTS

| | | | |
|---|---|---|---|
| 6,212,006 B1 | 4/2001 | Reiner | |
| 9,662,013 B2 | 5/2017 | Fukuma et al. | |
| 10,201,270 B2 | 2/2019 | Abt | |

(Continued)

FOREIGN PATENT DOCUMENTS

| | | |
|---|---|---|
| DE | 3539009 A1 | 5/1987 |
| DE | 4114646 A1 | 5/1992 |

(Continued)

OTHER PUBLICATIONS

Beale, J. A Surgical Stereo-Video Microscope, Ophthalic Surgery 1975, vol. 6, No. 1, pp. 22 to 26.

(Continued)

*Primary Examiner* — Mohammed A Hasan
(74) *Attorney, Agent, or Firm* — Walter Ottesen, P.A.

(57) ABSTRACT

An eye surgery visualization system includes an image sensor and contains an imaging system for producing an image of an object region with an optical imaging beam path in an imaging plane on an image sensor. A computer unit has an image processing routine for an image of the object region, the image having been captured by the image sensor. An image display unit visualizes image data of an image processed in the computer unit. An ophthalmoscopy loupe of the system images a portion lying within a patient's eye in an intermediate image plane that is conjugate to the imaging plane on the image sensor. The image processing routine separates the first portions of the image of the object region from second portions of the image of the object region in the imaging plane on the image sensor.

11 Claims, 5 Drawing Sheets

(56) References Cited

U.S. PATENT DOCUMENTS

2016/0007848 A1\* 1/2016 Filippatos ............ A61B 3/1225
　　　　　　　　　　　　　　　　　　　　　　　351/206
2019/0125182 A1\* 5/2019 Charles ................ A61B 3/0041

FOREIGN PATENT DOCUMENTS

| DE | 29905969 U1 | 7/1999 |
| DE | 102009030504 A1 | 12/2010 |
| DE | 102016203473 A1 | 9/2016 |
| WO | 9115150 A1 | 10/1991 |
| WO | 2017063714 A1 | 4/2017 |

OTHER PUBLICATIONS

Spandau, U. et al: Complications During and After Cataract Surgery, A Guide to Surgical Management, Springer-Verlag Berlin Heidelberg (published 2014), p. 260.

\* cited by examiner

EYE SURGERY VISUALIZATION SYSTEM

CROSS REFERENCE TO RELATED APPLICATION

This application claims priority of German patent application no. 10 2017 121 085.7, filed Sep. 12, 2017, the entire content of which is incorporated herein by reference.

FIELD OF THE INVENTION

The invention relates to an eye surgery visualization system comprising an image sensor, comprising an imaging system for producing an image of an object region with an optical imaging beam path in an imaging plane on the image sensor, comprising a computer unit, which contains an image processing routine for an image of the object region, the image having been captured by means of the image sensor and having an image plane, and comprising an image display device for visualizing image data of an image processed in the computer unit. The invention also relates to an eye surgery visualization system comprising a first image sensor, comprising an imaging system for producing an image of an object region with an optical imaging beam path in an imaging plane on the first image sensor, comprising a second image sensor, comprising a second imaging system for producing an image of an object region with an optical imaging beam path in an imaging plane on the second image sensor, comprising a computer unit, which contains an image processing routine for processing an image of the object region, the image having been captured by means of the first image sensor and having an image plane, and for processing an image of the object region, the image having been captured by means of the second image sensor and having an image plane, and comprising an image display device for visualizing image data of an image of the first image sensor and of the second image sensor, processed in the computer unit. Moreover, the invention relates to a method for providing image data for visualizing a patient's eye, and a computer program.

BACKGROUND OF THE INVENTION

An eye surgery visualization system including an image sensor and a computer unit, which contains an image processing routine for an image of the object region, the image having been captured by the image sensor, is known from DE 10 2009 030 504 A1.

Eye surgery visualization systems are used in ophthalmic surgery, for example in the case of surgical interventions on the rear portion of a patient's eye.

DE 41 14 646 A1 describes an eye surgery visualization system containing a surgical microscope with an ophthalmoscopy attachment module arranged below a microscope main objective along an extension of the microscope tube. This ophthalmoscopy attachment module contains one or more ophthalmoscopy loupes, which serve to produce an inverted image, that is, upside-down and back-to-front image, of the eye fundus of the patient's eye in a first intermediate image plane. By way of an optical system for image erection and pupil interchange, the image of this first intermediate image plane is erected and imaged laterally correctly into a second intermediate image plane. The image of this second intermediate image plane can be seen by an observer in the eye surgery visualization system through the microscope main objective and a displaceable lens that is arranged between the microscope main objective and the system for image direction and pupil interchange in the ophthalmoscopy attachment module. The ophthalmoscopy attachment module allows an observer to observe a region of interest in the interior of a patient's eye.

An observer examining an object region with an eye surgery visualization system using an ophthalmoscopy loupe is visually presented with an image of the object region that has different orientations in the portions within the ophthalmoscopy loupe and in the portions outside of the ophthalmoscopy loupe. A consequence thereof, in particular in so-called vitreoretinal surgery, is that portions of the object region seen through the ophthalmoscopy loupe are displayed to the observer laterally correctly whereas portions of the object region situated next to the ophthalmoscopy loupe do not experience laterally correct imaging from the view of the observer.

However, it is desirable that an observer can observe both areas of an object region that lie on the side of ophthalmoscopy loupes facing away from the microscope tube and areas that are not perceived through the ophthalmoscopy loupe with one and the same image orientation. This is because this ensures that the observer during an ophthalmological operation, in which the observer inserts an endoscopic light guide through a trocar into the patient's eye, need not move the light guide in a mirror-inverted manner in relation to the observation image. This is because if portions of the patient's eye are not displayed laterally correctly to the observer through the ophthalmoscopy loupe, the observer, that is, as a rule, the surgeon, perceives the feed of instruments into the operating area from the outside into the interior of the patient eye, that is, from the edge of the observation image to the centre thereof, differently in the case of a surgical operation with the eye surgery visualization system than what would correspond to the actual movement of the instruments.

SUMMARY OF THE INVENTION

Against this background, it is an object of the invention to provide an eye surgery visualization system which, independently of a set magnification, facilitates the observation of an object region with portions of a patient's eye arranged in the interior of the patient's eye, without an observation image with image portions having a different image orientation being visualized in the process.

The invention proposes the provision of an image sensor and an imaging system for producing an image of an object region with an optical imaging beam path in an imaging plane on the image sensor, and of a computer unit in an eye surgery visualization system, the computer unit containing an image processing routine for processing an image of the object region, the image having being captured by means of the image sensor and having an image plane. In the eye surgery visualization system, there is an image display device for visualizing image data of an image processed in the computer unit. The eye surgery visualization system contains an ophthalmoscopy loupe for imaging a portion lying within a patient's eye in an intermediate image plane that is conjugate to the imaging plane on the image sensor. The image processing routine serves to separate the first portions of the image of the object region, the first portions having been captured by means of the image sensor and produced by means of an imaging beam path passing through the ophthalmoscopy loupe, from second portions of the image of the object region in the imaging plane on the image sensor, the second portions having been captured by means of the image sensor and produced by means of an imaging beam path extending outside of the ophthalmoscopy loupe and being complementary to the first portions, to convert the first portions of the image of the object region into mirrored first portions in an automorphism corresponding to a mirroring of the first portions about two mirror axes that lie in the image plane of the image and that are perpendicular to one another, and to combine the mirrored first portions and the second portions that are complementary to the first portions to form a composed object region image that is fed to the image display.

Here, portions of the image of the object region that are complementary to one another are understood to mean image portions that are separated from one another and, when composed, yield the image of the object region.

An eye surgery visualization system according to the invention can also contain a first image sensor and an imaging system for producing an image of an object region with an optical imaging beam path in an imaging plane on the first image sensor, a second image sensor and a second imaging system for producing an image of an object region with an optical imaging beam path in an imaging plane on the second image sensor, and also a computer unit with an image processing routine for processing an image of the object region, the image having been captured by means of the first image sensor and having an image plane, and for processing an image of the object region, the image having been captured by means of the second image sensor and having an image plane. Then, there is an image display device for visualizing image data of an image of the first image sensor and of the second image sensor that was processed in the computer unit in this eye surgery visualization system. This eye surgery visualization system according to the invention likewise comprises an ophthalmoscopy loupe for imaging a portion lying within a patient's eye in an intermediate image plane that is conjugate to the imaging plane on the first image sensor and for imaging a portion lying within a patient's eye in an intermediate image plane that is conjugate to the imaging plane on the second image sensor. In the eye surgery visualization system, the image processing routine serves to separate the first portions of the respective image of the object region, the first portions having been captured by means of the first image sensor and the second image sensor and respectively produced by means of an imaging beam path passing through the ophthalmoscopy loupe, from second portions of the respective image of the object region in the imaging plane on the first and second image sensor, the second portions having been captured by means of the image sensors and respectively produced by means of an imaging beam path extending outside of the ophthalmoscopy loupe and being complementary to the first portions, to convert the respective first portions of the respective image of the object region into respectively mirrored first portions in an automorphism corresponding to a mirroring of the first portions about two mirror axes that lie in the image plane of the image and that are perpendicular to one another, and to respectively combine the mirrored first portions and the second portions that are complementary thereto to form a composed object region image that is fed to the image display device.

The magnification of the first imaging system and the magnification of the second imaging system can be the same or different.

According to the invention, provision can be made, for example, for the first imaging system to image the object region with a greater magnification than the second imaging system. In this way, it is possible to image the retina of a patient's eye in format-filling fashion on the first image sensor and to feed the image of the sclera of the patient's eye to the second image sensor. Here, it should be noted that, in the case of an eye surgery visualization system according to the invention, provision can be made for a first stereoscopic partial image of the object region to be captured by means of a plurality of first image sensors and a second stereoscopic partial image of the object region to be captured by means of a plurality of second image sensors, wherein the first stereoscopic partial image and the second stereoscopic partial image have different magnifications and wherein the first stereoscopic partial image and the second stereoscopic partial image are combined to form a stereoscopic overall image fed to the image display device.

In a preferred embodiment of the invention, provision is made for the image processing routine to contain an evaluation stage for image data which, depending on image information in the form of a portion of the retina of the patient's eye, triggers the exclusive processing of image data relating to the first portions of the image in a retina visualization routine, in which the first portions of the image of the object region are converted into mirrored first portions in an automorphism corresponding to a mirroring of the first portions about two mirror axes that lie in the image plane of the image and that are perpendicular to one another and are output to the image display device as a retina visualization routine object region image. In this way, it is possible to avoid the unnecessary processing of image data in two video streams if, for example, only the image of the retina of a patient's eye should be displayed as the object region image.

The image processing routine in the eye surgery visualization system may contain an algorithm for recognizing a lens edge of the ophthalmoscopy loupe by means of image processing, this algorithm defining the area in the image of the object region surrounded by the lens edge of the ophthalmoscopy loupe as first portions of the image of the object region that were produced with an imaging beam path passing through the ophthalmoscopy loupe.

The ophthalmoscopy loupe in the eye surgery visualization system is preferably held on an ophthalmoscopy loupe support that has at least one portion with a characteristic colour, wherein the algorithm for recognizing an edge of the ophthalmoscopy loupe contains a colour evaluation routine that is matched to the characteristic colour of the at least one portion of the ophthalmoscopy loupe support.

A preferred embodiment of the invention provides for the image processing routine to contain an algorithm for recognizing the pupil of the patient's eye by means of image processing and to define the area surrounded by the lens edge of the ophthalmoscopy loupe in the image of the object region as first portions of the image of the object region that were produced with an imaging beam path passing through the ophthalmoscopy loupe.

A method according to the invention for providing image data for visualizing a patient's eye comprises the steps of feeding an image of the patient's eye to an image processing routine and processing the image to form image data in an image processing routine. Here the image of the patient eye is captured with an imaging beam path at least partly passing through an ophthalmoscopy loupe. Here, the first portions of the image of the object region, the first portions having been captured by means of the image sensor and produced by means of an imaging beam path passing through the ophthalmoscopy loupe, are separated from second portions of the image of the object region in the imaging plane on the image sensor, the second portions having been captured by means of the image sensor and produced by means of an imaging beam path extending outside of the ophthalmoscopy loupe and being complementary to the first portions, wherein the first portions of the image of the object region are converted into mirrored first portions in an automorphism corresponding to a mirroring of the first portions about two mirror axes that lie in the image plane of the image and that are perpendicular to one another, and the mirrored first portions are combined with the second portions that are complementary to the first portions to form image data about a composed object region image.

A computer program according to the invention contains program code means for executing the method specified above on a computer unit.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
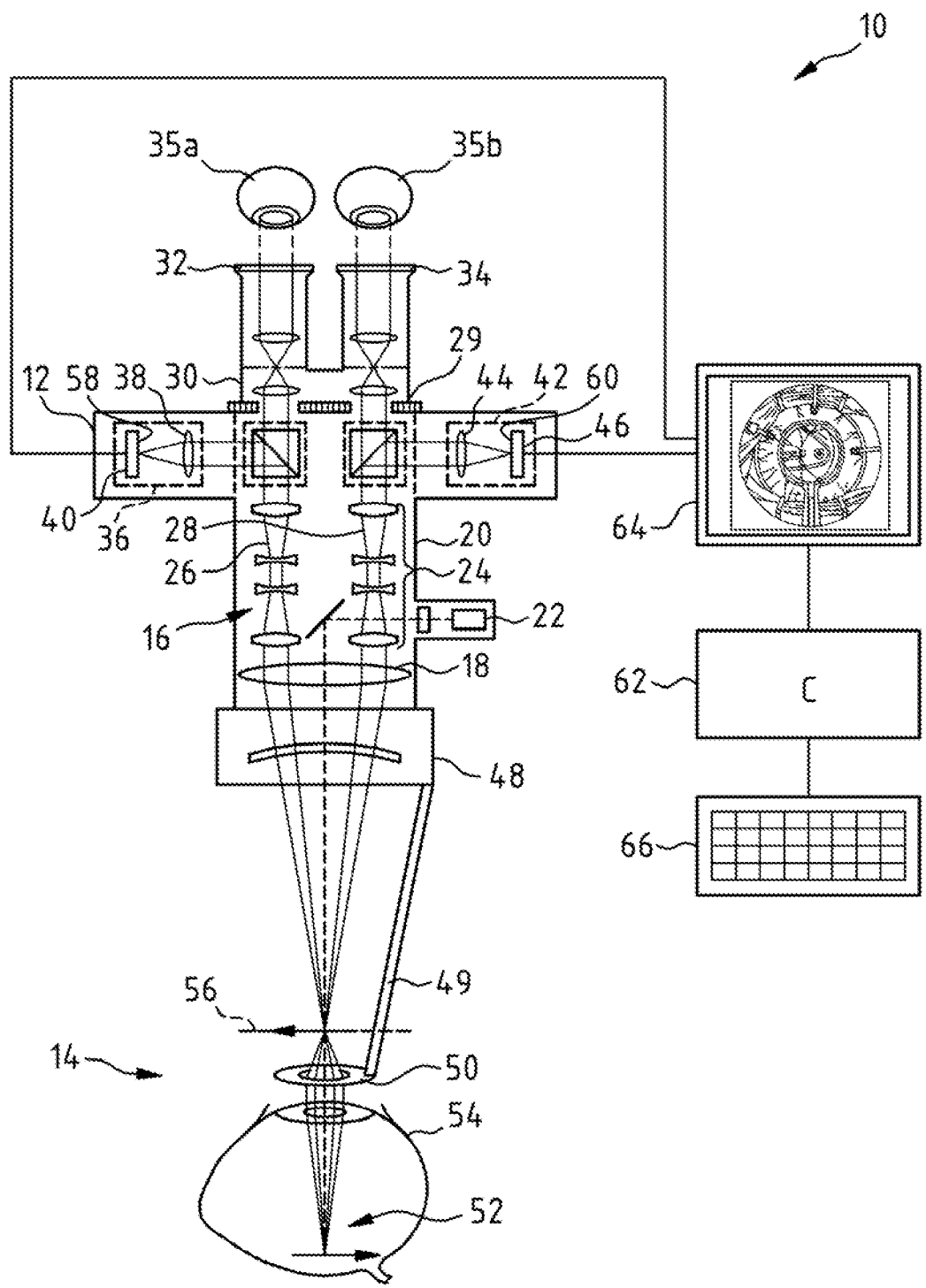
FIG. 1 shows a first eye surgery visualization system with a patient's eye.

The first eye surgery visualization system 10 shown in FIG. 1 contains a surgical microscope 12, which serves for the stereoscopic observation of an object region 14. The surgical microscope 12 comprises an imaging optical unit 16 with a microscope main objective system 18, this imaging optical unit being received in a main body 20. In the surgical microscope 12, there is an illumination device 22, which facilitates the illumination of the object region 14 with an illumination beam path 23, which passes through the microscope main objective system 18. The surgical microscope 12 has an afocal magnification system 24, through which a first stereoscopic partial observation beam path 26 and a second stereoscopic partial observation beam path 28 are guided. The surgical microscope 12 has a binocular tube 30 connected to an interface 29 of the main body 20, the binocular tube having a first eyepiece 32 and a second eyepiece 34 for a left and a right eye 35a, 35b of an observer. The microscope main objective system 18 in the surgical microscope 12 is traversed by the first stereoscopic partial observation beam path 26 and the second stereoscopic partial observation beam path 28. In the surgical microscope 12, there is a first image capture device 36 with a first objective lens system 38 and with a first image sensor 40. The image capture device 36 serves to capture image information from the first stereoscopic partial observation beam path 26. By means of a second image capture device 42, image information from the second stereoscopic partial observation beam path 28 can be captured in the surgical microscope 12. The second image capture device 42 has a second objective lens system 44 and contains a second image sensor 46.

An ophthalmoscopy attachment module 48 comprising an ophthalmoscopy loupe 50 that is received in an ophthalmoscopy loupe support 49 is connected to the surgical microscope 12. The ophthalmoscopy loupe 50 serves to image a portion 52 lying in the interior of the patient eye 54, through the natural lens and the cornea of the latter, into an intermediate image plane 56, which is conjugate to the imaging plane 58 on the first image sensor 40 and to the imaging plane 60 on the second image sensor 46.

The ophthalmoscopy loupe support 49 is stained to be green so that the latter can easily be distinguished from the hues of a patient's eye 54 and the hues of the surgical instruments used during ophthalmological surgery and is easily identifiable in the object region 14. It should be noted that the ophthalmoscopy loupe support 49 may also be stained yellow, in particular, in an alternative embodiment of the invention. The ophthalmoscopy loupe support 49 may also have any other suitable colouring rendering it possible for the latter to be easily seen in the object region 14 during ophthalmological surgery in relation to an image background with body fluids such as, for example, blood and body tissue and surgical instruments.

The eye surgery visualization system 10 has a computer unit 62 which contains an image processing routine for an image of the object region 14, the image having been captured by means of the first image sensor 40 and the second image sensor 46. Connected to the computer unit 62 as an image display device is a monitor 64 that is embodied for the visualization of 3-D image information. The computer unit 62 of the eye surgery visualization system 10 can be controlled by means of a keyboard 66 as an input interface.

It should be noted that, in a modified embodiment of the eye surgery visualization system, provision can also be made of a first and a second monitor for the visualization of 3-D image information. Then, an overview image of the object region, for example, can be displayed on the first monitor and a magnified portion of the patient's eye can be displayed on the second monitor.

Figure 2:
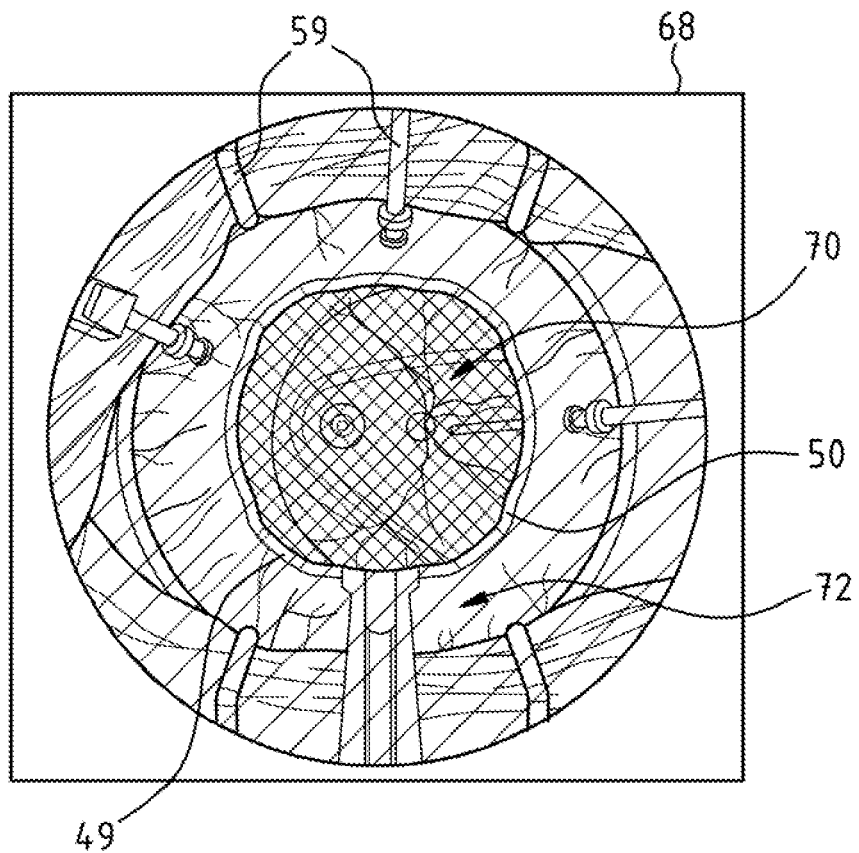
FIG. 2 shows an image of the patient's eye, captured with an image sensor in the eye surgery visualization system.

FIG. 2 shows an image 68 of the patient's eye in the imaging plane 58 with the ophthalmoscopy loupe 50 and with surgical instruments 59, this image having been captured by means of the image capture device 36. The image 68 has first portions 70, which are produced by means of an imaging beam path that passes through the ophthalmoscopy loupe 50, and has second portions 72, complementary thereto, which are caused by an imaging beam path that is guided past the ophthalmoscopy loupe 50 when coming from the object region 14.

The technical function of the image processing routine in the computer unit 62 consists, firstly, of separating the first portions of the image 68 of the object region 14, the first portions having been captured by means of the image capture device 36 on the image sensor 40 and produced by means of an imaging beam path passing through the ophthalmoscopy loupe 50, from second portions 72 of the image 68 of the object region 14 in the imaging plane 58 on the first image sensor 40, the second portions having been imaged on the first image sensor 40 and produced by means of an imaging beam path extending outside of the ophthalmoscopy loupe 50 and being complementary to the first portions 70. Correspondingly, the image processing routine in the computer unit 62 is configured to separate, that is, bring apart, the first portions of an image corresponding to the image 68 of the object region 14, the first portions having been captured by means of the second image capture device 42 and produced by means of an imaging beam path passing through the ophthalmoscopy loupe 50, from second portions 72 of an image corresponding to the image 68 of the object region 14 in the imaging plane 60 on the second image sensor 46, the second portions having been captured by means of the first image sensor 40 and produced by means of an imaging beam path extending outside of the ophthalmoscopy loupe 50 and being complementary to the first portions 70.

Moreover, a function of the image processing routine in the computer unit 62 lies in subjecting the first portions 70 of the image of the object region 14 to an image reversal operation since the image of the portion 52 arranged in the interior of the patient's eye 54, the image having been produced in the intermediate image plane 56 by means of the ophthalmoscopy loupe 50, is upside-down and back-to front, that is, inverted, in the intermediate image plane 56. Moreover, it is a function of the image processing routine in the computer unit 62 to combine the first portions 70 of the image of the object region 14 and the second portions 72 of the image of the object region 14 to form a composed, laterally correct and erect object image, which can then be displayed on the monitor 64 of the eye surgery visualization system 10.

Figure 3:
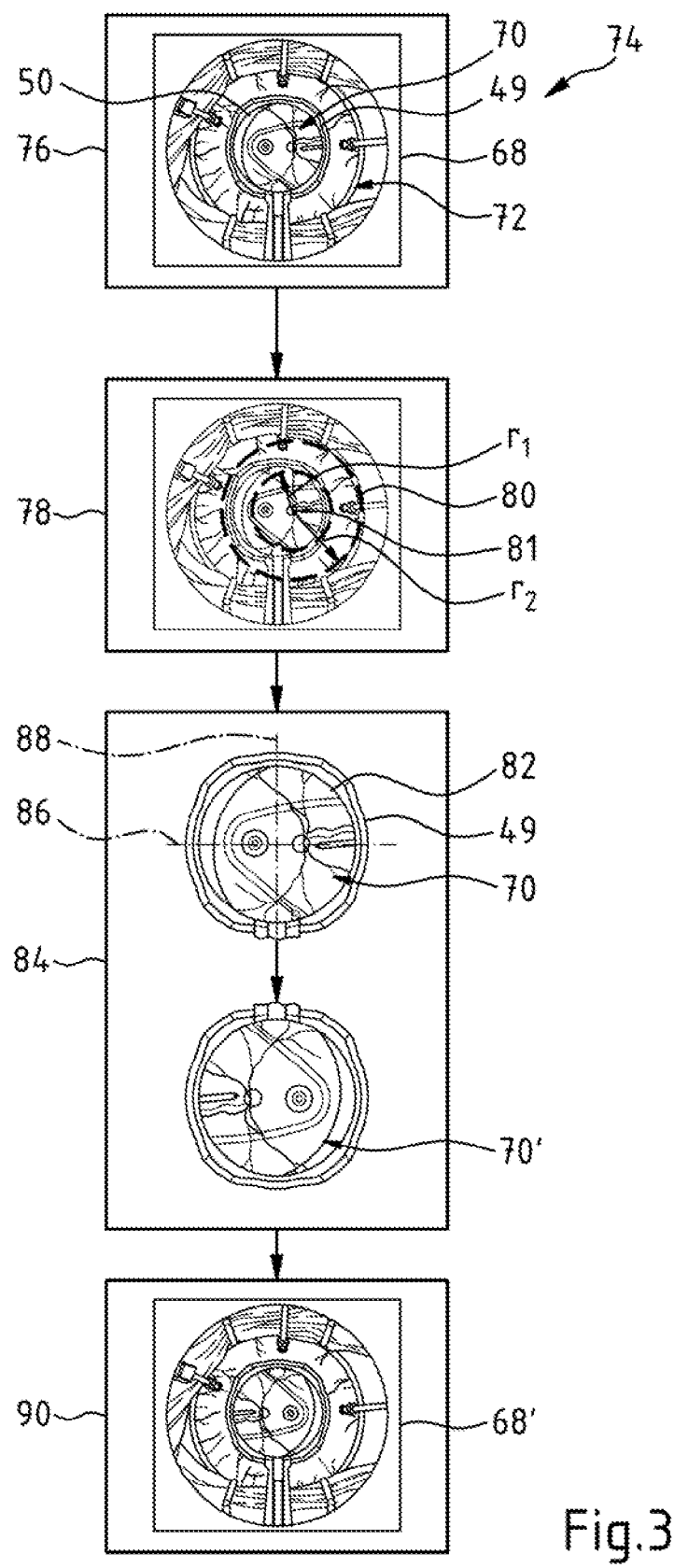
FIG. 3 shows a flowchart of an image processing routine of a computer unit of the eye surgery visualization system.

FIG. 3 shows a flowchart 74 for the image processing routine. The image processing routine in the computer unit 62 has an image portion separation stage 76, which is fed the image of an image sensor 40, 46. The image portion separation stage 76 of the image processing routine contains an algorithm for recognizing a lens edge of the ophthalmoscopy loupe 50, this algorithm recognizing the structure of the ophthalmoscopy loupe support 49 in the image fed to an image sensor 40, 46 by means of image processing. To this end, there is a colour evaluation function, which is matched to a characteristic colour of the ophthalmoscopy loupe support 49, in the algorithm of the image portion separation stage 76.

The image processing routine contains a filter stage 78. In the filter stage 78, the image portions of the image captured by an image sensor 40, 46 are then convolved by means of ring filters 80, wherein the filter centre 81 and the filter radii r1 and r2 are varied in the captured image in order then to determine a set of image points in the image therefrom, the set corresponding to the portion of the ophthalmoscopy loupe support 49 which surrounds the ophthalmoscopy loupe 50. The inner filter radius r1 of the ring filter 80 at which the convolution function assumes an extremal value is then determined as one edge 82 of the ophthalmoscopy loupe 50. On the basis of the edge 82 of the ophthalmoscopy loupe 50 determined in this way, the area of the first portions 70 of the image of the object region 14, shown in FIG. 2, is established in a subsequent step in order then to separate these first portions 70 from the area of the second portions 72 in the image of the object region 14, shown in FIG. 2, in a further step.

The first portions 70 of the image of the object region 14 separated from the second portions 72 of the image by means of the filter stage 78 are then fed to a mirroring stage 84 in the image processing routine. In the mirroring stage 84, the first portions 70 of the image of an image sensor 40, 46 are converted into mirrored first portions 70' by an automorphism by means of mirroring about two mirror axes 86, 88 that lie in the image plane of the image 68 and that are perpendicular to one another. It should be noted that, in an alternative embodiment, the automorphism of the mirroring routine can also be embodied as a rotation of the first portions 70 about an axis of rotation that is perpendicular to the image plane. Moreover, it is possible, for example, to provide point mirroring as such an automorphism.

The mirrored first portions 70' are then transferred in the image processing routine to a combination stage 90, in which the mirrored first portions 70' and the second portions 72 of an image of the object region 14, the image having been captured by means of the image sensors 40, 46, are composed again to form a composed object region image 68'. The image data of the composed image are then visualized on the monitor 64 as a stereoscopic image of the object region 14.

It should be noted that the image processing routine in the computer unit 62 may contain an evaluation stage for image data relating to image data captured by means of the first image sensor 40 or the second image sensor 46, the evaluation stage, depending on captured image information, for example, image information in the form of a portion of the retina of the patient's eye 54, suppressing the processing of image data provided by the first or the second image sensor 40, 46.

It should also be noted that if, for example, only the image of the retina of a patient's eye 54 is intended to be displayed as the object region image, unnecessary processing of image data can be avoided by virtue of the image processing routine containing a retina visualization routine which is triggered depending on captured image information and in which the first portions 70 of the respective image of the object region 14 are converted into mirrored first portions in an automorphism corresponding to a mirroring of the first portions about two mirror axes that lie in the image plane of the image and that are perpendicular to one another and are then output to the image display device in the form of a monitor 64 as a retina visualization routine object region image.

Figure 4:
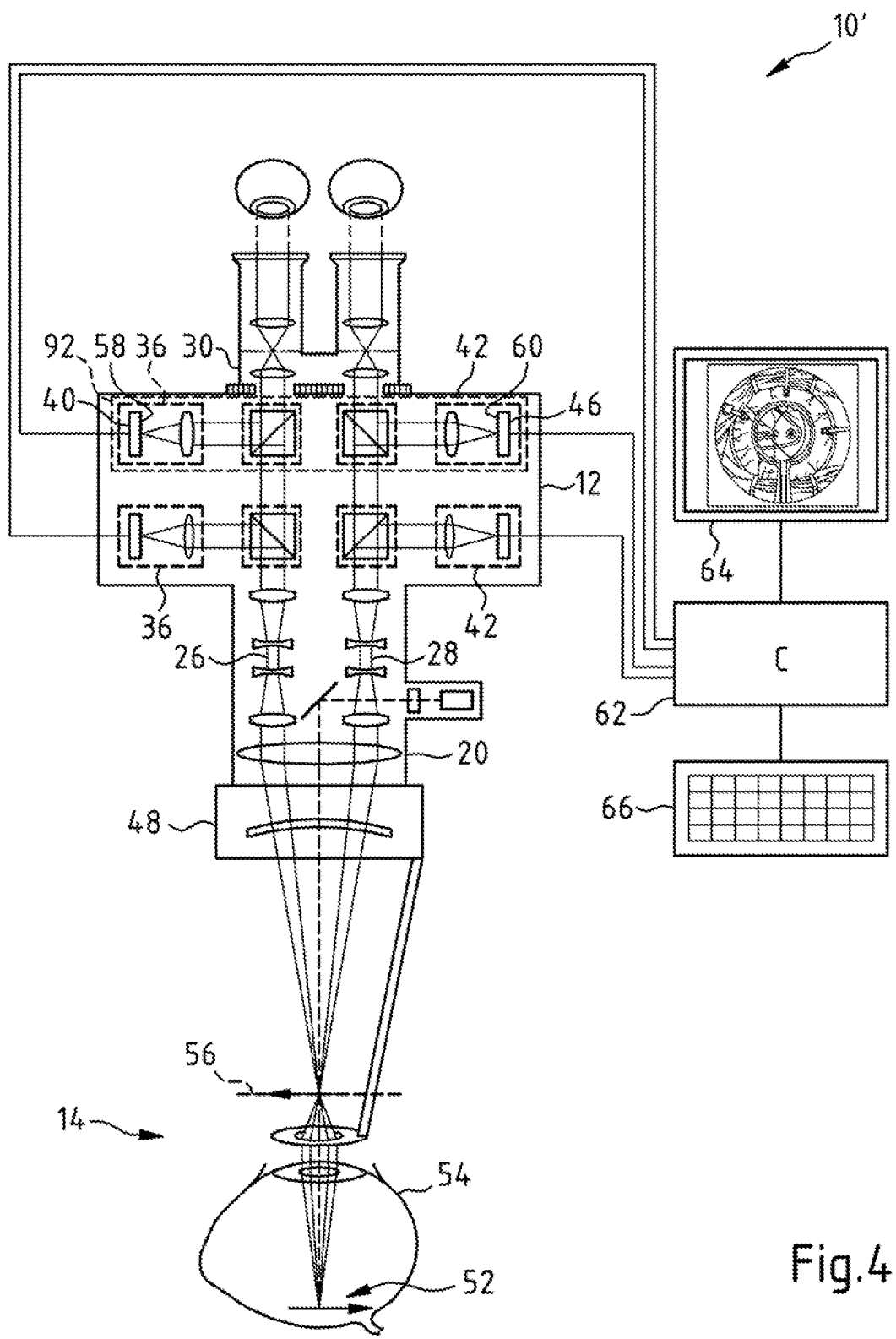
FIG. 4 shows a second eye surgery visualization system.

FIG. 4 shows a second eye surgery visualization system 10'. To the extent that assemblies and elements in the eye surgery visualization system 10' correspond to assemblies and elements in the eye surgery visualization system 10 described above, these are denoted by the same numbers as reference signs. In the eye surgery visualization system 10', there is a device for mirroring-in data 92, which is connected to the computer unit 62 and which facilitates the display of display information in the first and second stereoscopic partial observation beam path 26, 28 overlaid on an image of the object region 14 that is perceivable in the binocular tube 30.

Figure 5:
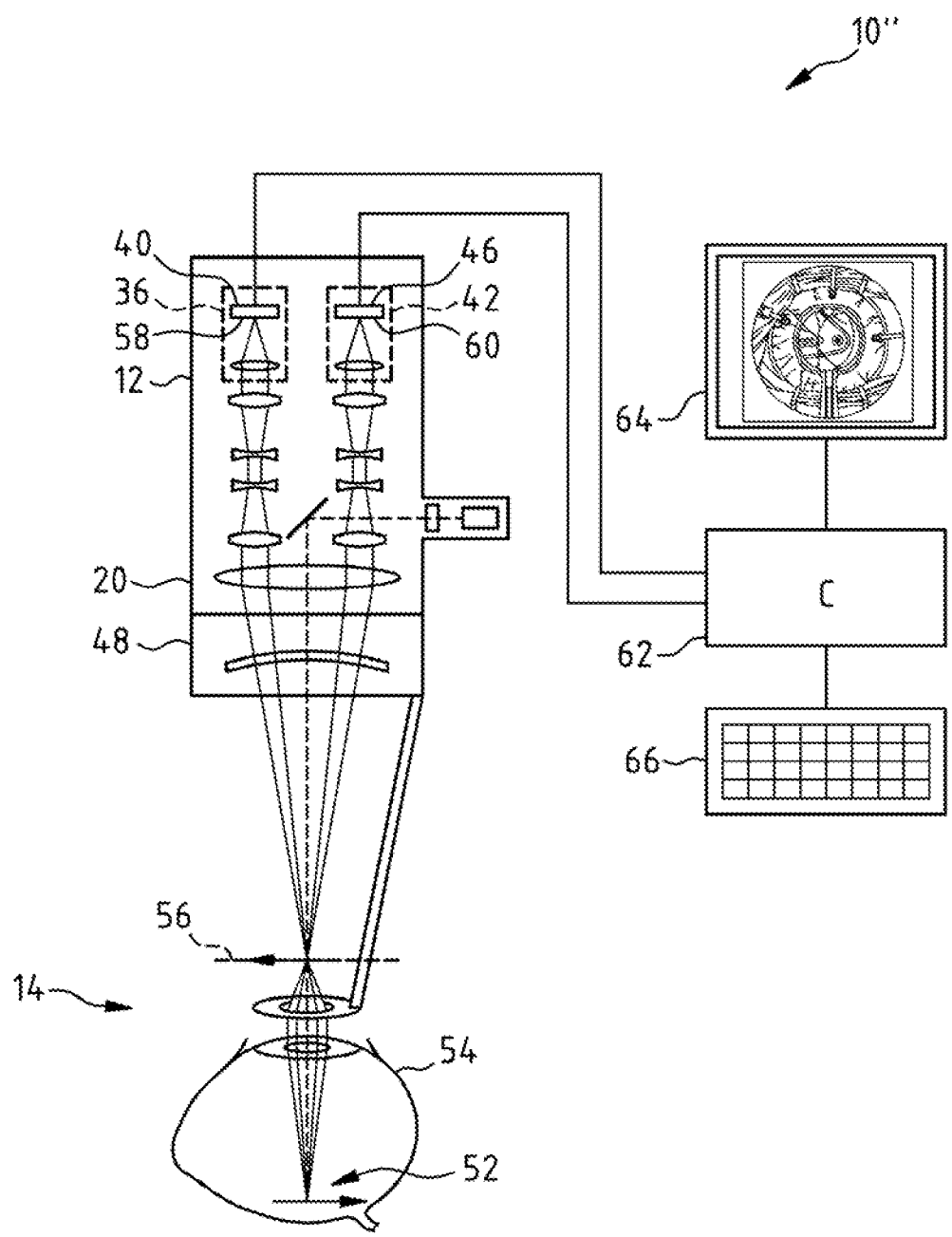
FIG. 5 shows a third eye surgery visualization system.

FIG. 5 shows a third eye surgery visualization system 10". To the extent that assemblies and elements in the eye surgery visualization system 10" correspond to assemblies and elements in the eye surgery visualization system 10 described above, these are denoted by the same numbers as reference signs. Unlike in the surgical microscope 12 of the eye surgery visualization system 10 and 10', the surgical microscope 12 of the eye surgery visualization system 10" is a purely digital surgical microscope for the stereoscopic capture of the object region 14 by means of a first image sensor 40 and a second image sensor 46.

Like the computer unit 62 of the first eye surgery visualization system 10, the computer unit 62 of the second and third eye surgery visualization system 10', 10" contains an image processing routine for processing the images of the object region, the images having been captured by means of the image sensors 40, 46, the image processing routine having the functionality described above on the basis of FIG. 3.

To sum up, the following preferred features of the invention should be noted in particular: An eye surgery visualization system 10 comprises an image sensor 40, 46 and comprises an imaging system for producing an image 68 of an object region 14 with an optical imaging beam path in an imaging plane 58, 60 on the image sensor 40, 46. The eye surgery visualization system 10 comprises a computer unit 62, which contains an image processing routine for an image 68 of the object region 14, the image having been captured by means of the image sensor 46 and having an image plane, and an image display device 64 for visualizing image data of an image 68 processed in the computer unit 62. According to the invention, the eye surgery visualization system 10, 10', 10" has an ophthalmoscopy loupe 50 for imaging a portion 52 lying within a patient's eye 54 in an intermediate image plane 56 that is conjugate to the imaging plane 58, 60 on the image sensor 40, 46. The image processing routine serves to separate the first portions 70 of the image 68 of the object region, the first portions having been captured by means of the image sensor 40, 46 and produced by means of an imaging beam path passing through the ophthalmoscopy loupe 50, from second portions 72 of the image 68 of the object region 14 in the imaging plane 60 on the image sensor 40, 46, the second portions having been captured by means of the image sensor 40, 46 and produced by means of an imaging beam path extending outside of the ophthalmoscopy loupe 50 and being complementary to the first portions, to convert the first portions 70 of the image 68 of the object region 14 into mirrored first portions 70' in an automorphism corresponding to a mirroring of the first portions 70 about two mirror axes 86, 88 that lie in the image plane of the image 68 and that are perpendicular to one another, and to combine the mirrored first portions 70' and the second portions 72 of the image 68 that are complementary to the first portions 70 to form a composed object region image that is fed to the image display.

It is understood that the foregoing description is that of the preferred embodiments of the invention and that various changes and modifications may be made thereto without departing from the spirit and scope of the invention as defined in the appended claims.

LIST OF REFERENCE SIGNS 10, 10', 10" Eye surgery visualization system
12 Surgical microscope
14 Object region
16 Imaging optical unit
18 Main microscope objective system
20 Main body
22 Illumination device
23 Illumination beam path
24 Afocal magnification system
26 First stereoscopic partial observation beam path
28 Second stereoscopic partial observation beam path
29 Interface
30 Binocular tube
32 First eyepiece
34 Second eyepiece
35a Left eye
35b Right eye
36 First image capture device
38 First objective lens system
40 First image sensor
42 Second image capture device
44 Second objective lens system
46 Second image sensor
48 Ophthalmoscopy attachment module
49 Ophthalmoscopy loupe support
50 Ophthalmoscopy loupe
52 Portion
54 Patient's eye
56 Intermediate image plane
58 Imaging plane
59 Surgical instrument
60 Imaging plane
62 Computer unit
64 Image display device (monitor)
66 Keyboard
68 Image
68' Composed object region image
70 First portions
70' Mirrored first portions
72 Second portions
74 Flowchart
76 Image portion separation stage
78 Filter stage
80 Ring filter
81 Filter centre
82 Edge
84 Mirroring stage
86, 88 Mirror axes
90 Combination stage
92 Mirroring-in data
r1, r2 Filter radii

What is claimed is:

1. An eye surgery visualization system comprising:
an image sensor;
an imaging system for producing an image of an object region with an optical imaging beam path in an imaging plane on the image sensor;
a computer unit containing an image processing routine for processing the image of the object region;
said image having been captured by said image sensor;
an image display unit for visualizing image data of an image processed in said computer unit;
an ophthalmoscopy loupe for imaging a section lying within a patient's eye in an intermediate image plane conjugated to the imaging plane on the image sensor;
said image processing routine being configured to separate first portions of the image of the object region from second portions of the image of the object region in the imaging plane on the image sensor;
said first portions having been captured by the image sensor and produced by an imaging beam path passing through the ophthalmoscopy loupe and said second portions having been captured by the image sensor and produced by an imaging beam path extending outside of the ophthalmoscopy loupe and being complementary to the first portions;
said image processing routine being further configured to convert the first portions of the image of the object region into mirrored first portions in an automorphism corresponding to a mirroring of the first portions about two mirror axes that lie in the image plane of the image of the object region and that are perpendicular to one another; and,
said image processing routine being further configured to combine the mirrored first portions and the second portions that are complementary to the first portions to form a composite object region image that is fed to said image display unit.

2. The eye surgery visualization system of claim 1, wherein the image processing routine further includes an evaluation stage for image data which, depending on image information in the form of a portion of the retina of the patient's eye, triggers the exclusive processing of image data relating to the first portions of the image in a retina visualization routine, in which the first portions of the image of the object region are converted into mirrored first portions in an automorphism corresponding to a mirroring of the first portions about two mirror axes that lie in the image plane of the image and that are mutually perpendicular and are output to the image display unit as a retina visualization routine object region image.

3. An eye surgery visualization system comprising:
a first image sensor;
an imaging system for producing an image of an object region with an optical imaging beam path in an imaging plane on the first image sensor;
a computer unit containing an image processing routine for processing the image of the object region;
said image having been captured by the first image sensor;
an image display unit for visualizing image data of an image of the first image sensor processed in the computer unit;
a second image sensor and a second imaging system for producing the image of an object region with an optical imaging beam path in an imaging plane on the second image sensor;
the image processing routine being configured to process the image of the object region, said image having been captured by the second image sensor;
said image display unit being configured to visualize image data of said image of the second image sensor processed in said computer unit;
an ophthalmoscopy loupe for imaging a section lying within a patient's eye in an intermediate image plane conjugated to the imaging plane on the first image sensor and for imaging the section lying within the patient's eye in an intermediate image plane conjugated to the imaging plane on the second image sensor;
said image processing routine being configured to separate the first portions of the image of the object region corresponding thereto from second portions of the corresponding image of the object region in the imaging plane on the first and second image sensor;
said first portions having been captured by the first image sensor and the second image sensor and respectively produced by an imaging beam path passing through the ophthalmoscopy loupe and said second portions having been captured by the image sensors and produced by an imaging beam path extending outside of the ophthalmoscopy loupe and being complementary to the first portions;
said image processing routine being further configured to convert the corresponding first portions of the image of the object region into respective mirrored first portions in an automorphism corresponding to a mirroring of the first portions about two mirror axes lying in the image plane of the image and being perpendicular to one another; and;
said image processing routine being further configured to respectively combine the mirrored first portions and the second portions that are complementary thereto to form a composite object region image that is fed to said image display unit.

4. The eye surgery visualization system of claim 3, wherein the image processing routine contains an evaluation stage for image data which, depending on image information in the form of a portion of the retina of the patient's eye, triggers the exclusive processing of image data relating to the first portions of the corresponding image of the object region in a retina visualization routine, in which the first portions of the respective image of the object region are converted into mirrored first portions in an automorphism corresponding to a mirroring of the first portions about two mirror axes lying in the image plane of the image and being perpendicular to one another and then output to the image display device as a corresponding retina visualization routine object region image.

5. The eye surgery visualization system of claim 4, wherein the first imaging system images the object region with a greater magnification than the second imaging system.

6. The eye surgery visualization system of claim 3, wherein the first image sensor functions to capture a first stereoscopic partial image of the object region and the second image sensor functions to capture a second stereoscopic partial image of the object region and the image display device is configured for the stereoscopic visualization of image data of the image, processed in the computer unit, of the first image sensor and of the second image sensor.

7. The eye surgery visualization system of claim 3, wherein the image processing routine contains an algorithm for recognizing a lens edge of the ophthalmoscopy loupe by image processing and defines the area surrounded by the edge of the ophthalmoscopy loupe in the image of the object region as first portions of the image of the object region that were produced with an imaging beam path passing through the ophthalmoscopy loupe.

8. The eye surgery visualization system of claim 7, wherein the ophthalmoscopy loupe is held on an ophthalmoscopy loupe support and the algorithm for recognizing an edge of the ophthalmoscopy loupe contains a color evaluation routine that is matched to a characteristic color of at least one portion of the ophthalmoscopy loupe support.

9. The eye surgery visualization system of claim 3, wherein the image processing routine contains an algorithm for recognizing the pupil of the patient's eye by image processing and defines the area surrounded by the lens edge of the ophthalmoscopy loupe in the image of the object region as first portions of the image of the object region that were produced with an imaging beam path passing through the ophthalmoscopy loupe.

10. A method for providing image data for visualizing a patient's eye, the method comprising the steps of:
feeding an image of a patient's eye to an image processing routine;
processing the image to form image data in an image processing routine;
capturing the image of the patient's eye with an imaging beam path at least partly passing through an ophthalmoscopy loupe;
producing first portions of said image of the patient's eye with an imaging beam path passing through the ophthalmoscopy loupe and producing said second portions of said image of the patient's eye with an imaging beam path extending outside of the ophthalmoscopy loupe and being complementary to the first portions;
separating the captured first portions of the image of the object region from the second portions of the image of the patient's eye;
converting the first portions of the image of the object region into mirrored first portions in an automorphism corresponding to a mirroring of the first portions about two mirror axes that lie in an image plane of the image and that are perpendicular to one another and the mirrored first portions are combined with the second portions that are complementary to the first portions to form image data about a composite object region image.

11. A computer program having program code means for executing the method specified in claim 10 on a computer unit.

\* \* \* \* \*